United States Patent
Tsukagoshi

(10) Patent No.: US 11,821,016 B2
(45) Date of Patent: Nov. 21, 2023

(54) METHOD FOR CULTURING BACILLUS BACTERIUM, AND METHOD FOR PRODUCING USEFUL SUBSTANCE

(71) Applicant: IDEMITSU KOSAN CO., LTD., Chiyoda-ku (JP)

(72) Inventor: Yuki Tsukagoshi, Chiyoda-ku (JP)

(73) Assignee: SDS BIOTECH K.K., Tokyo (JP)

( * ) Notice: Subject to any disclaimer, the term of this patent is extended or adjusted under 35 U.S.C. 154(b) by 0 days.

(21) Appl. No.: 16/339,861

(22) PCT Filed: Oct. 6, 2017

(86) PCT No.: PCT/JP2017/036440
§ 371 (c)(1),
(2) Date: Apr. 5, 2019

(87) PCT Pub. No.: WO2018/066688
PCT Pub. Date: Apr. 12, 2018

(65) Prior Publication Data
US 2019/0241924 A1    Aug. 8, 2019

(30) Foreign Application Priority Data
Oct. 7, 2016  (JP) ................... 2016-199419

(51) Int. Cl.
C12P 21/00 (2006.01)
C12N 1/20 (2006.01)
C12P 1/00 (2006.01)

(52) U.S. Cl.
CPC ............... *C12P 21/00* (2013.01); *C12N 1/20* (2013.01); *C12P 1/00* (2013.01)

(58) Field of Classification Search
CPC .............. C12P 21/00; C12P 1/00; C12N 1/20
USPC ........................................... 435/243
See application file for complete search history.

(56) References Cited

U.S. PATENT DOCUMENTS

| | | | |
|---|---|---|---|
| 5,621,089 A | 4/1997 | Sloma et al. | |
| 5,856,167 A | 1/1999 | Outtrup | |
| 6,010,898 A | 1/2000 | Paik et al. | |
| 2008/0050779 A1* | 2/2008 | Defachelles | C12N 1/14 435/71.1 |
| 2008/0124771 A1 | 5/2008 | Kim et al. | |
| 2009/0175837 A1 | 7/2009 | Yuki et al. | |
| 2019/0048311 A1 | 2/2019 | Eguchi et al. | |

FOREIGN PATENT DOCUMENTS

| | | |
|---|---|---|
| CA | 911351 A | 10/1972 |
| CN | 1946297 A | 4/2007 |
| CN | 101411389 | * 4/2009 |
| CN | 103937712 A | 7/2014 |
| JP | 6-254584 A | 9/1994 |
| JP | 9-502097 A | 3/1997 |
| JP | 11-103855 A | 4/1999 |
| JP | 11-504813 A | 5/1999 |
| JP | 2003-235593 A | 8/2003 |
| JP | 2007-236286 A | 9/2007 |
| JP | 2010-510776 A | 4/2010 |
| WO | WO 2016/163534 A1 | 10/2016 |

OTHER PUBLICATIONS

Ozturk et al., Fed-Batch Biomolecule Production by Bacillus subtilis: A State of the Art Review, Trends in Biotechnology, vol. 34, No. 4, (Apr. 2016), pp. 329-345.*
International Search Report dated Dec. 26, 2017 in PCT/JP2017/036440 filed Oct. 6, 2017.
Pawut Kanjanachumpol, et al., "Enhancing polyhydroxybutrate production from high cell density fed-batch fermentation of *Bacillus megaterium* BA-019," Bioprocess Biosyst Eng. vol. 36, 2013, pp. 1463-1474.
Ting Gao, et al., "L-lactic acid production by *Bacillus subtillis* MUR1," Bioresource Technology, vol. 121, 2012, pp. 105-110.
R. R. Farrera, et al., "Carbon:nitrogen ratio interacts with initial concentration of total solids on insecticidal crystal protein and spore production in *Bacillus thuringiensis* HD-73," Appl Microbiol Biotechnol, vol. 49, 1998, pp. 758-765.
Wan Salwanis Wad Md. Zain, et al., "Production of cyclowdextrin glucanotransferase from alkalophilic *Bacillus* sp. TS1-1: Optimization of carbon and nitrogen concentration in the feed medium using central composite design," Biochemical Engineering Journal, vol. 33, 2007, pp. 26-33.
S. M. S. Monterio, et al., "Enhanced Spore Production of *Bacillus subtilis* Grown in a Chemically Defined Medium," Advances in Microbiology, vol. 4, 2014, pp. 444-454.
Extended European Search Report dated Jun. 8, 2020 in Patent Application No. 17858524.6, 8 pages.
R. R. Fonseca, et al., "Optimizing Carbon/Nitrogen Ratio for Biosurfactant Production by a Bacillus Subtillis Strain" Applied Biochemistry and Biotechnology, vol. 136-140, 2007, pp. 471-486.

* cited by examiner

Primary Examiner — Jennifer M. H. Tichy
(74) Attorney, Agent, or Firm — Oblon, McClelland, Maier & Neustadt, L.L.P.

(57) ABSTRACT

An objective of the present invention is to provide a culturing method, by which *Bacillus* bacterial spores can be efficiently produced. The present invention provides a method for producing *Bacillus* bacterial spores, comprising culturing *Bacillus* bacteria in a liquid medium containing a sugar or a sugar-source raw material at a concentration between 50.1 g/L and 100 g/L at the start of culture, and then in the course of the culture, feeding a fed-batch medium containing a sugar or a sugar-source raw material and a nitrogen-containing compound, and having the weight ratio (C/N ratio) of carbon atoms to nitrogen atoms ranging from 5.5 to 13.5 to the liquid medium.

10 Claims, No Drawings

METHOD FOR CULTURING BACILLUS BACTERIUM, AND METHOD FOR PRODUCING USEFUL SUBSTANCE

TECHNICAL FIELD

The present invention relates to a method for culturing *Bacillus* bacteria.

BACKGROUND ART

*Bacillus* bacteria or active components produced by *Bacillus* bacteria are broadly used in many fields of food, medicines, and livestock industry, etc. Particularly for microbial pesticides or medicines for intestinal disorders containing viable cells as active components, distribution and use of *Bacillus* bacteria in the form of spores are considered as common ways in view of durability and stability.

In general, liquid media mainly containing a carbon source such as sugars, a nitrogen source such as amino acids and inorganic ammonium salts, and minerals, for example, is used for culturing *Bacillus* bacteria.

Non Patent document 1 discloses that when *Bacillus* bacteria were cultured by batch culture in a liquid medium containing these components, spores were obtained at about 3.5E+09 spore/ml.

Patent document 1 discloses that high concentrations of *Bacillus* bacterial spores could be obtained through culturing under the conditions of a step of using media containing up to 5, 10, 20, 10, and 20% of saccharides, a yeast extract, a dried corn steep liquor product, soy peptone and a concentrated shochu distillery by-product, respectively, and adjusting the oxygen concentration on and after the logarithmic growth phase to 10% or less. However, oxygen is desired to be present sufficiently in the system for the growth of *Bacillus* bacteria, and some strains of *Bacillus* bacteria grow poorly when cultured under the hypoxic conditions in the logarithmic growth phase. Hence, bacteria to which the method is applicable are limited.

Patent document 2 discloses a method of enhanced production of protease, which involves culturing protease-producing *Bacillus* bacteria in a medium containing high concentrations of a sugar-source raw material and a nitrogen source. However, the method involves culturing by batch culture, so that a limited amount of protease is obtained by a single culture.

In general, when a higher concentration of spores or metabolites is obtained via a single treatment, a culture method that involves increasing the concentration of nutritional substrates in media is generally applied. However, such a method is problematic in that when *Bacillus* bacteria are cultured with increasing amounts of substrates assimilable by *Bacillus* bacteria, the bacterial cell concentration and metabolites increase in proportion thereto, and when culturing is continued even after the concentrations of the substrates exceed given levels, the culture system becomes unable to adequately oxygenate due to the increased oxygen demand, leading to poor growth and longer time required for culturing, for example. Non Patent Document 1 reports that particularly the culturing of *Bacillus* bacteria in a medium containing glucose at a concentration higher than 20 g/L inhibits sporulation.

Accordingly, fed-batch culture (semi-batch culture) is performed to obtain high concentrations of *Bacillus* bacterial spores and metabolites via a single treatment without inhibiting the sporulation of *Bacillus* bacteria. This technique involves adding a nutritional substrate that has disappeared during the culture process at an appropriate concentration and appropriate timing, so that bacterial cells and metabolites can be obtained at concentrations higher than those in the case of adding no such substrate.

Non Patent Document 1 discloses that fed-batch culture improved the productivity of bacterial cells to a degree significantly higher than that of batch culture, and a high concentration of *Bacillus* bacterial spores was obtained. However, the document demonstrates that sporulation is inhibited by the use of a medium containing 20 g/L or more of glucose. Specifically, in the document, a sugar concentration is lowered at the start of culture, and a sugar-source raw material and a nitrogen source are fed in a manner such that the concentrations thereof remain at low levels. This increases the time for adding these materials and finally results in as long as 60 hours of the culture time. Moreover, regarding medium components used herein, the medium contains chemically pure compounds in combination, and is a complete synthetic medium. Hence, a huge cost is required to obtain spores through large-scale culturing of *Bacillus* bacteria for industrial application. Therefore, it is desired to culture using residues discharged in a step of large-scale production of food or the like, or a raw material made of a mixture such as defatted soy flour or yeast extract, the production of which does not require much labor. However, a method for efficiently obtaining *Bacillus* bacterial spores using a medium containing high concentrations of these materials has never been reported.

Patent document 3 discloses a method that involves feeding glucose at predetermined intervals to a medium according to glucose consumption during culturing in such a manner that the final concentration of glucose is 1%. For culturing *Bacillus* bacteria, the addition of a nitrogen-containing compound simultaneously with the feeding of saccharides is more advantageous for growth.

Patent document 4 discloses a method that involves culturing *Bacillus licheniformis* by fed-batch culture in a medium containing a high concentration of a sugar for production of 3-hydroxybutyrate, and being composed of carbon atoms and nitrogen atoms at a weight ratio (C/N ratio) between 12.4 and 24. However, culturing of *Bacillus* bacteria in a medium containing sugars at a concentration higher than a required level is inappropriate to obtain a high concentration of *Bacillus* bacterial spores.

PRIOR ART REFERENCES

Patent Documents

Patent Document 1: JP2007-236286A
Patent Document 2: JP H11-103855A (1999)
Patent Document 3: JP H06-254584A (1994)
Patent Document 4: JP H09-502097A (1997)

Non Patent Document

Non Patent Document 1: Advances in Microbiology, 2014, 4, 444-454

SUMMARY OF THE INVENTION

Problems to be Solved by the Invention

As described above, *Bacillus* bacteria should be cultured under conditions where a culture substrate is fed in a proper quantity required for generation of the high concentrations of spores and metabolites of *Bacillus* bacteria, in order to quickly obtain the high concentrations of *Bacillus* bacterial spores and useful substances such as the metabolites by liquid culture. Accordingly, finding of new conditions that satisfy such needs has been demanded. Therefore, an object of the present invention is to provide a culturing method by which spores and useful substances such as metabolites can be efficiently produced from *Bacillus* bacteria from which high concentrations of spores and metabolites could not easily be obtained by conventional liquid medium for bacteria.

Means for Solving the Problems

As a result of intensive studies to solve the above problems, the present inventors have discovered that fed-batch culture is performed by feeding a medium prepared to be composed of a carbon source containing a sugar or a sugar-source raw material and a nitrogen source containing an ammonium salt, ammonia or defatted soy flour and corn steep liquor etc., at predetermined proportions of the components, to a medium with a high concentration of a sugar-source raw material at the initial stage of culture, so as to be able to grow *Bacillus* bacteria without inhibiting the growth, and, to obtain high concentrations of *Bacillus* bacterial spores and useful substances such as metabolites, which have been unable to be obtained by conventional methods. Thus, the present inventors have completed the present invention.

The present invention is as follows.

[1] A method for culturing a *Bacillus* bacterium, comprising culturing a *Bacillus* bacterium in a liquid medium containing a sugar or a sugar-source raw material the concentration of which is between 50.1 g/L and 100 g/L at the start of culture, and then in the course of the culture, feeding a fed-batch medium to the liquid medium, wherein said fed-batch medium contains a sugar or a sugar-source raw material and a nitrogen-containing compound, and has a weight ratio (C/N ratio) of carbon atoms to nitrogen atoms between 5.5 and 13.5.

[2] The method for culturing a *Bacillus* bacterium according to [1], comprising culturing a *Bacillus* bacterium by feeding a fed-batch medium having a weight ratio (C/N ratio) of carbon atoms to nitrogen atoms between 5.5 and 12 to the liquid medium.

[3] The method for culturing a *Bacillus* bacterium according to [1] or [2], wherein the total amount of the sugar or the sugar-source raw material to be fed from the fed-batch medium till the end of culture is 100 g or less per liter of the medium before feeding.

[4] The method for culturing a *Bacillus* bacterium according to any one of [1] to [3], wherein the fed-batch medium is fed at a timing in a seven-hour-time period prior to or after the time point when the oxygen consumption rate of *Bacillus* bacteria is maximal.

[5] The method for culturing a *Bacillus* bacterium according to any one of [1] to [4], wherein the fed-batch medium is fed at a timing in a time period of from three hours to thirty hours after the start of culture.

[6] The method for culturing a *Bacillus* bacterium according to any one of [1] to [5], wherein the fed-batch medium is obtained by heat-sterilizing a solution containing the sugar or the sugar-source raw material and the nitrogen-containing compound.

[7] The method according to any one of [1] to [6], wherein the sugar or the sugar-source raw material is a non-reducing sugar.

[8] The method for culturing a *Bacillus* bacterium according to [7], wherein the non-reducing sugar is at least one sugar selected from the group consisting of sucrose, trehalose, kestose, melezitose, gentianose, neobifurcose, fungitetraose, planteose, raffinose, stachyose, and bifurcose.

[9] The method for culturing a *Bacillus* bacterium according to any one of [1] to [8], wherein the nitrogen-containing compound is at least one compound selected from the inorganic nitrogen compound group consisting of ammonium salts and ammonia, and the organic nitrogen compound group consisting of amino acids, peptides, proteins, urea, defatted soy flour, soybean-derived components, yeast-derived components, corn steep liquor, dry powder of corn steep liquor, corn-derived components, animal and plant proteins and hydrolysates thereof.

[10] The method for culturing a *Bacillus* bacterium according to any one of [1] to [9], wherein a dissolved oxygen concentration in the liquid medium is kept at 10% or more.

[11] The method for culturing a *Bacillus* bacterium according to any one of [1] to [10], wherein the temperature of the liquid medium is regulated between 20° C. and 60° C. to control the growth of the *Bacillus* bacterium.

[12] The method for culturing a *Bacillus* bacterium according to [11], wherein the *Bacillus* bacterium is cultured at 28° C. to 32° C. during the logarithmic growth phase, and then cultured at 35° C. to 39° C.

[13] The method for culturing a *Bacillus* bacterium according to any one of [1] to [12], wherein the *Bacillus* bacterium is selected from the group consisting of *Bacillus subtilis, Bacillus amyloliquefaciens, Bacillus pumilus, Bacillus simplex, Bacillus lentus, Bacillus laterosporus, Bacillus alvei, Bacillus popilliae, Bacillus licheniformis, Bacillus brevis, Bacillus stearothermophilus, Bacillus alcalophilus, Bacillus coagulans, Bacillus circulans, Bacillus siamensis, Bacillus lautus, Bacillus clausii, Bacillus megaterium, Bacillus thuringiensis, Bacillus cereus, Bacillus firmus, Bacillus velezensis, Bacillus pichinotyi, Bacillus acidocaldarius, Bacillus alkalicola, Bacillus azotoformans, Bacillus anthracis, Bacillus badius, Bacillus bataviensis, Bacillus cycloheptanicus, Bacillus aneurinilyticus, Bacillus migulanus, Bacillus abyssalis, Bacillus aestuarii, Bacillus polymyxa,* and *Bacillus* sp.

[14] A method for producing a useful substance, comprising producing a useful substance is a liquid medium by using the culturing method according to any one of [1] to [13].

[15] The method for producing a useful substance according to [14], wherein the useful substance is a spore of the *Bacillus* bacterium.

[16] The method for producing a useful substance according to [14], wherein the useful substance is a metabolite of the *Bacillus* bacterium.

[17] The method for producing a useful substance according to [16], wherein the metabolite is a cyclic lipopeptide.

[18] The method for producing a useful substance according to [17], wherein the cyclic lipopeptide is at least one cyclic lipopeptide selected from the group consisting of iturin, surfactin, plipastatin, fengycin, bacillomycin, lichenysin, kurstakin, mycosubtilin, colistin, fusaricidin, paenibacterin, polymyxin and pumilacidin.

Effect of the Invention

According to the present invention, *Bacillus* bacteria can be grown to a high bacterial concentration and thus spores and useful substances such as metabolites can be produced at high rates.

EMBODIMENTS FOR CARRYING OUT THE INVENTION

The method for culturing a *Bacillus* bacterium of the present invention comprises culturing a *Bacillus* bacterium in a liquid medium containing a sugar or a sugar-source raw material the concentration of which is between 50.1 g/L and 100 g/L at the start of culture, and then in the course of the culture, feeding a fed-batch medium to the liquid medium, wherein the fed-batch medium contains a sugar or a sugar-source raw material and a nitrogen-containing compound, and has the weight ratio (C/N ratio) of carbon atoms to nitrogen atoms ranging from 5.5 to 13.5.

By using the method for culturing *Bacillus* bacteria of the present invention, spores and useful substances such as metabolites can be generated at high rates in the liquid medium.

Examples of *Bacillus* bacteria to be used in the present invention are not particularly limited, as long as they are bacteria classified as the genus *Bacillus*, and include *Bacillus subtilis*, *Bacillus amyloliquefaciens*, *Bacillus pumilus*, *Bacillus simplex*, *Bacillus lentus*, *Bacillus laterosporus*, *Bacillus alvei*, *Bacillus popilliae*, *Bacillus licheniformis*, *Bacillus brevis*, *Bacillus stearothermophilus*, *Bacillus alcalophilus*, *Bacillus coagulans*, *Bacillus circulans*, *Bacillus siamensis*, *Bacillus lautus*, *Bacillus clausii*, *Bacillus megaterium*, *Bacillus thuringiensis*, *Bacillus cereus*, *Bacillus firmus*, *Bacillus velezensis*, *Bacillus pichinotyi*, *Bacillus acidocaldarius*, *Bacillus alkalicola*, *Bacillus azotoformans*, *Bacillus anthracis*, *Bacillus badius*, *Bacillus bataviensis*, *Bacillus cycloheptanicus*, *Bacillus aneurinilyticus*, *Bacillus migulanus*, *Bacillus abyssalis*, *Bacillus aestuarii*, *Bacillus polymyxa*, and *Bacillus* sp.

In the present invention, the term "useful substances" refers to substances exhibiting bioactivity such as effects of accelerating animal and plant growth, bactericidal or bacteriostatic action, and effects of activating genes, industrially applicable substances such as various enzymes, lactic acid, and amino acid, and fermented products themselves to be used as food such as fermented soybeans and yogurt. Specific examples thereof include *Bacillus* bacterial spores and the metabolites of *Bacillus* bacteria. The metabolites of *Bacillus* bacteria are active components other than viable cells, which are produced via culturing, and examples thereof include cyclic peptides having antibiotic activity and surface activity and enzymes such as protease and lipase.

Examples of a cyclic lipopeptide that is a metabolite of *Bacillus* bacteria include at least one cyclic lipopeptide selected from the group consisting of iturin, surfactin, plipastatin, fengycin, bacillomycin, lichenysin, kurstakin, mycosubtilin, colistin, fusaricidin, paenibacterin, polymyxin and pumilacidin.

A medium to be used for culturing *Bacillus* bacteria contains at least a carbon source and a nitrogen source.

A carbon source that can be catabolized by *Bacillus* bacteria can be used for culturing. Examples of such a catabolizable carbon source include sugars that can be catabolized by *Bacillus* bacteria (such as glucose, lactose, glycerol, arabinose, ribose, xylose, galactose, fructose, mannose, inositol, mannitol, sorbitol, glucosamine, N-acetylglucosamine, cellobiose, maltose, sucrose, trehalose, and xylitol) or sugar-source raw materials. The term "sugar-source raw material" is a substrate that liberates the above catabolizable sugars by an enzyme such as amylase or cellulase produced by many microorganisms including *Bacillus* bacteria and refers to a raw material such as polysaccharides including starch, cellulose, pectin, and chitin, etc., and biomass such as rice straw, straw, chaff, food wastes, wood resulting from construction, and remainder materials of sawmills. Of these examples, a non-reducing sugar is preferable, and specific examples thereof include at least one non-reducing sugar selected from the group consisting of sucrose, trehalose, kestose, melezitose, gentianose, neobifurcose, fungitetraose, planteose, raffinose, stachyose and bifurcose.

A nitrogen source that can be catabolized by *Bacillus* bacteria can be used for culturing. Examples of such a catabolizable nitrogen source include nitrogen-containing compounds such as amino acids, peptides, animal and plant proteins and hydrolysates thereof, urea, soybean-derived components e.g., defatted soy flour, yeast-derived components, corn steep liquor, dry powder of corn steep liquor, corn-derived components, ammonium salts e.g., ammonium nitrate, ammonium sulfate, ammonium chloride, and ammonium acetate, ammonia, sodium nitrate, potassium nitrate, sodium glutamate, and urea.

Other medium components, such as trace metal salts commonly used for culturing *Bacillus* bacteria, may be added as long as they do not adversely affect sporulation and production of useful substances such as metabolites, and if necessary, for example, amino acids or vitamins may be added.

The amount of a sugar or a sugar-source raw material to be contained in a medium at the start of culture ranges from 50.1 to 100 g/L. When *Bacillus* bacteria are cultured, and particularly when *Bacillus* bacteria are cultured in a medium containing a sugar or a sugar-source raw material at such a high concentration, *Bacillus* bacteria is capable of growing more actively at the initial stage of culture, while such a sugar or a sugar-source raw material is efficiently consumed during growth without remaining at the late stage of culture, so that sporulation and the production of useful substances such as metabolites can be efficiently induced. In addition, culturing in a medium having the concentration of less than 50.1 g/L causes the sugar source to be completely consumed early and sporulation to proceed before sufficient growth. Moreover, culturing in a medium having the concentration of higher than 100 g/L inhibits growth and sporulation. It is required to culture with a medium composition containing a sugar or a sugar or a sugar-source raw material within the above range.

The amount of a nitrogen-containing compound to be contained in a medium at the start of culture preferably ranges from 8 to 72 g/L, and the C/N ratio of a medium at the start of culture preferably ranges from 5.5 to 13.5.

The above medium containing a sugar, or a sugar-source raw material and a nitrogen-containing compound can also be used as a fed-batch medium to be fed during culture. However, in the present invention, the weight ratio (C/N ratio) of carbon atoms to nitrogen atoms in a fed-batch medium is adjusted so that it ranges from 5.5 to 13.5, and preferably 5.5 to 12. By the adjustment of the C/N ratio within this range, production of high concentrations of spores and useful substances such as metabolites can be realized without inhibiting bacterial growth. On the other hand, culturing in a medium containing a high proportion of a sugar or a sugar-source raw material (C/N ratio exceeds 13.5) causes the sugar or the sugar-source raw material to remain in the medium at the end of culture. Such remaining sugar is known to inhibit sporulation of viable *Bacillus* bacterial cells. Furthermore, culturing in a medium containing a high proportion of a nitrogen source compound (C/N ratio is less than 5.5) leads to the shortage of a carbon source required for growth and thus is disadvantageous.

The C/N ratio is calculated as follows: C/N ratio=sum of carbon contents in each medium component/sum of nitrogen contents in each medium component.

The content of carbon that is a natural raw material among medium components can be roughly calculated to be 40% by weight of the total sugar amount and 50% by weight of the total protein amount. The total sugar amount can be determined as reducing sugar concentration by Somogyi method after 2.5 hours of hydrolysis in acid at 100° C. The total protein amount can be roughly calculated by determining the total nitrogen amount by Kjeldahl method and then multiplying the amount by the conversion factor, 6.25.

The amount of a medium to be fed before the end of culture is not particularly limited. Preferably, the total amount of a sugar or a sugar-source raw material to be fed from a fed-batch medium is 100 g or less per liter of the medium before feeding.

A fed-batch medium is preferably obtained by heat sterilization of a solution containing a non-reducing sugar or a non-reducing-sugar-containing sugar-source raw material and a nitrogen-containing compound.

Medium components are generally subjected to heat sterilization such as autoclave sterilization before the start of culture. However, when autoclave is performed under the conditions where a reducing sugar and a nitrogen source coexist, they serve as substrates to cause Maillard reaction, nutritive components required for growth are converted to other compounds, and the nutrition sources lose their original functions. This makes efficient growth of *Bacillus* bacteria difficult, so that sufficient bacterial cells and useful substances such as metabolites cannot be obtained. Accordingly, a general method involves performing heat sterilization of a sugar source and heat sterilization of a nitrogen source, separately, cooling sufficiently, mixing the two, and then subjecting the mixture to culturing. This mixing step is problematic in that it opens a system that has been maintained under the sterile conditions, increasing the risk of contamination and increasing necessary facilities and operation processes.

By contrast, the method of the present invention involves the use of a non-reducing sugar such as sucrose, so as to cause no Maillard reaction etc., even if a carbon source and a nitrogen source are simultaneously subjected to heat sterilization, and thus to facilitate the preparation of a medium.

A fed-batch medium may be fed only once or multiple times, such as 2 to 6 times intermittently. A fed-batch medium is preferably fed continuously in accordance with the consumption rate of nutrition sources.

A fed-batch medium is fed preferably at time points when *Bacillus* bacteria grow actively and consume oxygen and nutrition sources more actively. If the addition is initiated at the initial stage of culture, the concentrations of nutrients increase, the growth becomes active, oxygen is quickly consumed to result in insufficient oxygenation, and poor growth is caused by osmotic effect. Moreover, a prolonged cultivation time is required for obtaining sufficient spores and useful substances such as metabolites if feeding is performed after the period during which growth is active. In general, sporulation takes place upon nutrient depletion. If feeding is continued by the late stage of culture, the culture substrate remains in a large amount in the medium and thus no spore is formed. Therefore, for example, a fed-batch medium is fed preferably at a timing in a seven-hour-time period prior to or after the time point when the oxygen consumption rate of microorganisms is maximal (for example, at the time point when 8 hours has passed after the start of culture), and preferably at a timing in a time period of from three hours to thirty hours after the start of culture. More preferably, the feeding of a fed-batch medium is initiated between 5 to 20 hours after the start of culture, and then completed between 13 and 25 hours after the start of culture. The total cultivation time ranges from 24 to 48 hours, for example.

In addition, real-time monitoring of dissolved oxygen concentration in a culture medium is possible using a diaphragm galvanic electrode sensor or the like.

Culture conditions may be the conditions that are generally employed for liquid culture of *Bacillus* bacteria. For example, the growth of *Bacillus* bacteria is preferably controlled by regulating the temperature between 20° C. and 60° C., and preferably between 20° C. and 40° C., for example. For example, more efficient sporulation can be realized by culturing at 28° C. to 32° C., and preferably within 30° C.±1° C. during the logarithmic growth phase to control the growth of *Bacillus* bacteria and the consumption of a sugar or a sugar-source raw material, followed by culturing at 35° C. to 39° C., and preferably within 37° C.±1° C.

Moreover, culturing under the aerobic conditions (for example, oxygen concentration of 10% or more and preferably of 15% to 50%) with agitation is preferable, and the pH of the medium preferably ranges from 6.5 to 8.5, and more preferably ranges from 7.0 to 8.0.

The preculture may be performed before culturing in a liquid medium containing the sugar or the sugar-source raw material at a concentration between 50.1 g/L and 100 g/L.

As described above, *Bacillus* bacterial cells having a high sporulation rate (for example, 50% or more, preferably 80% or more) and metabolites of *Bacillus* bacteria can be obtained. *Bacillus* bacterial cells having such a high sporulation rate and metabolites of *Bacillus* bacteria can be used for desired purposes after adequate operation such as condensation or removal and drying of media.

EXAMPLES

The present invention will be described in detail below with reference to Examples, but is not limited to the following Examples.

Table 1 shows the compositions of media used in Examples, Reference Examples and Comparative Examples. The carbon contents of glucose, sucrose, and CSL among medium components were each calculated as 40% by weight of the total sugar amount and 50% by weight of the total protein amount. The total sugar amount was determined by determining the reducing sugar concentration by Somogyi method after 2.5 hours of hydrolysis in acid at 100° C. The total protein amount was determined by determining the total nitrogen amount by the Kjeldahl method, and then multiplying the total nitrogen amount by conversion factor, 6.25.

TABLE 1

| | MEDIUM CONDITION | | | | |
|---|---|---|---|---|---|
| | 1 | 2 | 3 | 4 | 5 |
| g/L Glucose | 12.5 | 50 | 0 | 0 | 250 |
| Sucrose | 0 | 0 | 50 | 250 | 0 |
| CSL [powder] | 15 | 60 | 60 | 90 | 90 |
| $MnCl_2 \cdot 4H_2O$ | 0.09 | 0.36 | 0.36 | 1.8 | 1.8 |
| $KH_2PO_4$ | 0.25 | 1 | 1 | 5 | 5 |
| C amount (g/L) | 8.70 | 34.8 | 34.8 | 72.19 | 72.19 |
| N amount (g/L) | 1.05 | 4.20 | 4.20 | 6.31 | 6.31 |
| C/N | 8.28 | 8.28 | 8.28 | 11.45 | 11.45 |
| Total sugar amount(g/L) | 13.4 | 56 | 56 | 280 | 280 |

Reference Example 1. Comparison of Sugar-Source Raw Materials (Glucose and Sucrose)

Each 100 ml of media containing glucose (Wako Pure Chemicals), CSL (ROQUETTE), $MnCl_2$ (Wako Pure Chemicals), and $KH_2PO_4$ (Wako Pure Chemicals) was prepared in a 500 ml Erlenmeyer flask, such that the final concentrations were as listed in medium condition 1 of Table 1 and then autoclave sterilization was carried out (glucose was separately sterilized and aseptically mixed). One loopful of *Bacillus subtilis* MBI-600 was taken from a colony grown on a nutrient agar plate, aseptically inoculated into the medium described in the medium condition 1 of Table 1 and cultured overnight with shaking at 30° C. and 150 rpm to obtain a preculture liquid.

Using a 5 L culture tank, each 2 L of two media was prepared such that the final concentrations were as listed in medium condition 2 (test No. 2) and 3 (test No. 3) of Table 1, and then autoclave sterilization was carried out (glucose was separately sterilized and aseptically mixed and sucrose (Wako Pure Chemicals) was mixed in advance with all medium components, followed by sterilization of the mixture).

Each 100 ml from the preculture liquid of the *Bacillus subtilis* MBI-600 obtained as described above was aseptically inoculated into a 5 L culture tank to start culturing under the condition of 30° C. and 500 rpm, and the oxygen supply was adjusted so as to prevent the dissolved oxygen concentration from falling below 10%. The term "dissolved oxygen concentration" refers to a numerical value representing by percentage the amount of oxygen dissolved in a culture medium per unit volume, and can be measured using an apparatus such as a tabletop culture apparatus (MDL-8C) (B. E. MARUBISHI CO., LTD.).

After 34 hours of culture, the thus obtained culture liquids were diluted with sterile water, and then applied to ordinary bouillon agar media (Eiken Chemical Co., Ltd.), followed by overnight static culture at 37° C. The numbers of the thus formed colonies were counted to count the numbers of cells. Furthermore, a previously prepared dilute solution was heated at 80° C. for 30 minutes and then similarly applied to an ordinary bouillon agar medium, followed by overnight static culture at 37° C. The number of the thus formed colonies was counted to count the number of heat-resistant bacteria. The sporulation rates were calculated from these results and shown in Table 2.

TABLE 2

| MEDIUM CONDITIONS | 2 | 3 |
|---|---|---|
| NUMBER OF CELLS (cfu/ml) | 1.50E+10 | 1.36E+10 |
| NUMBER OF HEAT-RESISTANT CELLS (cfu/ml) | 1.39E+10 | 1.29E+10 |
| SPORULATION RATE | 92.22% | 95.04% |

In this culture test, no significant difference was confirmed in the number of heat-resistant bacteria between media containing glucose as a carbon source sterilized separately from a nitrogen source and media containing sucrose as a carbon source sterilized simultaneously with a nitrogen source, in which *Bacillus subtilis* MBI-600 had been cultured.

Example 1. Comparison of the Number of Bacteria Cultured by Fed-Batch Culture

Each 100 ml of media was prepared in a 500 ml Erlenmeyer flask, such that the final concentrations were adjusted as listed in medium condition 1 of Table 1 and then autoclave sterilization was carried out (glucose was separately sterilized and aseptically mixed). One loopful of *Bacillus subtilis* MBI-600 was taken from a colony grown on a nutrient agar plate, aseptically inoculated into the medium and cultured overnight with shaking at 30° C. and 150 rpm to obtain a preculture liquid.

Using a 5 L culture tank, each 2 L of two media was prepared such that the final concentrations were as listed in medium condition 3 of Table 1, and then autoclave sterilization was carried out (all medium components were mixed in advance and then subjected to autoclave sterilization).

Using a 500 mL Duran bottle, one 0.4 L of medium was prepared such that the final concentrations were as listed in medium condition 4 of Table 1. The bottle was connected in advance via a tube so that the medium can be fed to the 5 L culture tank containing the medium of medium condition 3, and then autoclave was carried out (all medium components were mixed in advance and then subjected to autoclave sterilization).

Each 100 ml from the obtained preculture liquid was aseptically inoculated into each 5 L culture tank containing the above 2 L of medium to start culturing under the condition of 37° C. Five hours after the start of culture, the medium of medium condition 4 was added every 2 hours in an amount of 100 mL per addition in 4 divided additions to one of the 5 L culture tanks. After the start of addition, the culture temperature was lowered to 30° C. for culturing. At this time, the oxygen supply was adjusted by controlling the number of revolutions so as to prevent the dissolved oxygen concentration in each culture medium from falling below 10%. The oxygen consumption rate was maximal at about 8 hours after the start of culture. Twenty-four hours after the start of culture, the culture temperature was lowered to 37° C. for culturing.

After 34 hours of culture, the thus obtained culture liquids were diluted with sterile water, and then applied to ordinary bouillon agar media, followed by overnight static culture at 37° C. The numbers of the thus formed colonies were counted to count the numbers of cells. Furthermore, the previously prepared dilute solution was heated at 80° C. for 30 minutes and then similarly applied to an ordinary bouillon agar medium, followed by overnight static culture at 37° C. The number of the thus formed colonies was counted to count the number of heat-resistant bacteria. The sporulation rates were calculated from these results and shown in Table 3.

TABLE 3

| MEDIUM CONDITIONS | 3 | 3 + 4 |
|---|---|---|
| NUMBER OF CELLS (cfu/ml) | 1.36E+10 | 1.87E+10 |
| NUMBER OF HEAT-RESISTANT CELLS (cfu/ml) | 1.29E+10 | 1.83E+10 |
| SPORULATION RATE | 95.04% | 97.90% |

In this culture test, a 1.5-fold increase was found in the bacterial concentration of and an increase was found in heat-resistant spores of *Bacillus subtilis* cultured by fed-batch culture in media containing sucrose as a carbon source, in which all medium components had been simultaneously sterilized, compared with those of *Bacillus subtilis* not subjected to fed-batch culture.

Example 2. Culture Test Using Media Containing Simultaneously-Sterilized Reducing Sugar or Non-Reducing Sugar Each 100 ml of media was prepared in a 500 ml Erlenmeyer flask, such that the final concentrations were adjusted as listed in medium condition 1 of Table 1 and then autoclave sterilization was carried out (glucose was separately sterilized and aseptically mixed). One loopful of *Bacillus subtilis* MBI-600 was taken from a colony grown on a nutrient agar plate, aseptically inoculated into the medium and cultured overnight with shaking at 30° C. and 150 rpm to obtain a preculture liquid.

Each 2 L of media was prepared in a 5 L culture tank such that the final concentrations were as listed in medium condition 2 and 3 of Table 1 (glucose and sucrose were mixed in advance with all medium components and then sterilization was carried out).

Using a 500 mL Duran bottle, each 0.4 L of media was prepared such that the final concentrations were adjusted as listed in medium condition 4 and 5 of Table 1. The bottles were connected in advance via tubes, so that the medium of medium condition 4 could be fed to a 5 L culture tank containing the medium of medium condition 2, the medium of medium condition 5 could be fed to a 5 L culture tank containing the components of medium condition 3, and then autoclave was carried out (glucose and sucrose were mixed in advance with all medium components and then sterilization was carried out).

Each 100 ml from the obtained preculture liquid was aseptically inoculated into a 5 L culture tank containing the above 2 L of medium to start culturing under the condition of 37° C. Five hours after the start of culture, the medium of medium condition 4 was added to the medium of medium condition 3 and the medium of medium condition 5 was added to the medium of medium condition 2 every 2 hours in an amount of 100 mL per addition in 4 divided additions. After the start of addition, the culture temperature was lowered to 30° C. for culturing. At this time, the oxygen supply was adjusted by controlling the number of revolutions, so as to prevent the dissolved oxygen concentration in each culture medium from falling below 10%. When feeding was started, the glucose concentration of the culture medium cultured with medium condition 2 was below 40 g/L, and the oxygen consumption rate was maximal at about 8 hours after the start of culture. Twenty-four hours after the start of culture, the culture temperature was lowered to 37° C. for culturing.

After 34 hours of culture, the thus obtained culture liquids were diluted with sterile water, and then applied to ordinary bouillon agar media, followed by overnight static culture at 37° C. The numbers of the thus formed colonies were counted to count the numbers of cells. Furthermore, the previously prepared dilute solution was heated at 80° C. for 30 minutes and then similarly applied to an ordinary bouillon agar medium, followed by overnight static culture at 37° C. The number of the thus formed colonies was counted to count the number of heat-resistant bacteria. The sporulation rates were calculated from these results and shown in Table 4.

TABLE 4

| MEDIUM CONDITIONS | 3 + 4 | 2 + 5 |
|---|---|---|
| NUMBER OF CELLS (cfu/ml) | 1.87E+10 | 1.85E+10 |
| NUMBER OF HEAT-RESISTANT CELLS (cfu/ml) | 1.83E+10 | 1.48E+10 |
| SPORULATION RATE | 97.90% | 80.30% |

In this culture test, the bacterial concentration of *Bacillus subtilis*; that is, the number of sporulating bacteria obtained by fed-batch culture in media containing glucose as a carbon source, in which all medium components had been simultaneously sterilized, was lower than that of *Bacillus subtilis* cultured by fed-batch culture using sucrose as a carbon source.

Example 3. Fed-Batch Culture Test for *Bacillus thuringiensis*

Each 100 ml of media was prepared in a 500 ml Erlenmeyer flask, such that the final concentrations were adjusted as listed in medium condition 1 of Table 1 and then autoclave sterilization was carried out (glucose was separately sterilized and aseptically mixed). One loopful of *Bacillus thuringiensis* NBRC 101235 was taken from a colony thereof grown on a nutrient agar plate, aseptically inoculated into the medium and cultured overnight with shaking at 30° C. and 150 rpm to obtain a preculture liquid.

Each 2 L of a total of three media was prepared in a 5 L culture tank such that the final concentrations were adjusted as listed in medium condition 2 of Table 1 (glucose was separately sterilized and aseptically mixed).

Using a 500 mL Duran bottle, each 0.4 L of media was prepared such that the final concentrations were adjusted as listed in medium condition 4 and 5 of Table 1. The bottles were connected in advance via tubes, so that the media of medium condition 4 and 5 could be separately fed to 5 L culture tanks containing the medium of medium condition 2, and then autoclave was carried out (glucose was separately sterilized and aseptically mixed, and sucrose was mixed in advance with all medium components and then sterilization was carried out). The medium of medium condition 2, which was not subjected to fed-batch culture, was used as a control.

Each 100 ml from the obtained preculture liquid was aseptically inoculated into each 5 L culture tank containing the above 2 L of medium to start culturing under the condition of 37° C. Six hours after the start of culture, the medium of medium condition 4 or 5 was added to each of the two media in 5 L culture tanks every 2 hours in an amount of 100 mL per addition in 4 divided additions. After the start of addition, the culture temperature was lowered to 30° C. for culturing. At this time, the oxygen supply was adjusted by controlling the number of revolutions, so as to prevent the dissolved oxygen concentration in each culture medium from falling below 10%, as well as a 10% hydrochloric acid aqueous solution and a 2M sodium hydroxide solution were added to each fermentor, so as to regulate the pH of each culture medium during culture to range from 6.7 to 7.3. When feeding was started, the glucose concentration of the culture medium cultured with medium condition 2 was below 40 g/L, and the oxygen consumption rate was maximal at about 8 hours after the start of culture. Twenty-four hours after the start of culture, the culture temperature was increased to 37° C. for culturing.

After 34 hours of culture, the thus obtained culture liquids were diluted with sterile water, and then applied to ordinary bouillon agar media, followed by overnight static culture at 37° C. The numbers of the thus formed colonies were counted to count the numbers of cells. Furthermore, the previously prepared dilute solution was heated at 80° C. for 30 minutes and then similarly applied to an ordinary bouillon agar medium, followed by overnight static culture at 37° C. The number of the thus formed colonies was counted to count the number of heat-resistant bacteria. The sporulation rates were calculated from these results and shown in Table 5.

TABLE 5

| MEDIUM CONDITIONS | 2 | 2 + 5 | 2 + 4 |
|---|---|---|---|
| NUMBER OF CELLS (cfu/ml) | 1.25E+09 | 1.33E+09 | 1.74E+09 |
| NUMBER OF HEAT-RESISTANT CELLS (cfu/ml) | 1.19E+09 | 1.22E+09 | 1.61E+09 |
| SPORULATION RATE | 95.1% | 91.6% | 92.6% |

In this culture test, *Bacillus thuringiensis* was cultured by fed-batch culture, so that the thus obtained number of heat-resistant spores was greater than those obtained under the conditions where no feeding had been carried out. Furthermore, the number of heat-resistant spores obtained by feeding of media containing sucrose that is a non-reducing sugar was greater than those obtained by feeding of media containing glucose that is a reducing sugar.

Comparative Example 1. Fed-Batch Culture Using Only a Carbon Source

Each 100 ml of media was prepared in a 500 ml Erlenmeyer flask, such that the final concentrations were adjusted as listed in medium condition 1 of Table 1 and then autoclave sterilization was carried out (glucose was separately sterilized and aseptically mixed). One loopful of *Bacillus subtilis* MBI-600 was taken from a colony thereof grown on a nutrient agar plate, aseptically inoculated into the medium and cultured overnight with shaking at 30° C. and 150 rpm to obtain a preculture liquid.

One 2 L of medium was prepared in a 5 L culture tank such that the final concentrations were as listed in medium condition 2 of Table 1 and then autoclave sterilization was carried out (glucose was separately sterilized and aseptically mixed).

Using a 500 mL Duran bottle, one 0.4 L of medium was prepared such that the final concentration of glucose was 125 g/L. The bottle was connected in advance via a tube, so that the medium could be fed to the 5 L culture tank containing the medium of medium condition 2, and then autoclave was carried out (glucose was separately sterilized and aseptically mixed).

The obtained 100 ml of preculture liquid was aseptically inoculated into the above medium to start culturing under the condition of 37° C. Five hours after the start of culture, a glucose solution was added every 2 hours in an amount of 100 mL per addition in 4 divided additions. After the start of addition, the culture temperature was lowered to 30° C. for culturing. At this time, the oxygen supply was adjusted by controlling the number of revolutions, so as to prevent the dissolved oxygen concentration in the culture medium from falling below 10%. When feeding was started, the glucose concentration of the culture medium cultured with medium condition 2 was below 40 g/L, and the oxygen consumption rate was maximal at about 8 hours after the start of culture. Twenty-four hours after the start of culture, the culture temperature was increased to 37° C. for culturing.

After 34 hours of culture, the thus obtained culture liquids were diluted with sterile water, and then applied to ordinary bouillon agar media, followed by overnight static culture at 37° C. The numbers of the thus formed colonies were counted to count the numbers of cells. Furthermore, the previously prepared dilute solution was heated at 80° C. for 30 minutes and then similarly applied to an ordinary bouillon agar medium, followed by overnight static culture at 37° C. The number of the thus formed colonies was counted to count the number of heat-resistant bacteria. The sporulation rate was calculated from these results and shown in Table 6.

TABLE 6

| MEDIUM CONDITIONS | 2 + Glu |
|---|---|
| NUMBER OF CELLS (cfu/ml) | 1.39E+10 |
| NUMBER OF HEAT-RESISTANT CELLS (cfu/ml) | 1.13E+10 |
| SPORULATION RATE | 81.29% |

In this culture test, the bacterial concentration; that is, the thus obtained spore concentration of *Bacillus subtilis* cultured via feeding of only glucose as a carbon source was found to be lower than that of the case (2+5 in Table 4) of fed-batch culture using the medium simultaneously containing a carbon source and a nitrogen source.

Example 4. Comparison of the Amount of Iturin Resulting from Culture by Fed-Batch Culture Each 100 ml of media was prepared in a 500 ml Erlenmeyer flask, such that the final concentrations were adjusted as listed in medium condition 1 of Table 1 and then autoclave sterilization was carried out (glucose was separately sterilized and aseptically mixed). One loopful of *Bacillus subtilis* MBI-600 was taken from a colony thereof grown on a nutrient agar plate, aseptically inoculated into the medium and cultured overnight with shaking at 30° C. and 150 rpm to obtain a preculture liquid.

Each 2 L of two media was prepared in a 5 L culture tank such that the final concentrations were as listed in medium condition 2 of Table 1 and then autoclave sterilization was carried out (all medium components were mixed in advance and then subjected to autoclave sterilization).

Using a 500 mL Duran bottle, one 0.4 L of medium was prepared such that the final concentrations were as listed in medium condition 4 of Table 1. The bottle was connected in advance via a tube, so that the medium could be fed to each 5 L culture tank containing the medium of medium condition 2, and then autoclave was carried out (all medium components were mixed in advance and then subjected to autoclave sterilization).

Each 100 ml from the obtained preculture liquid was aseptically inoculated into each 5 L culture tank containing 2 L of the above medium of medium condition 2 to start culturing under the condition of 30° C. Five hours after the start of culture, the medium of medium condition 4 was added to one of the 5 L culture tanks every 2 hours, in an amount of 100 mL per addition in 4 divided additions, and culturing was continued. At this time, the oxygen supply was adjusted by controlling the number of revolutions, so as to prevent the dissolved oxygen concentration in the culture medium from falling below 10%. The oxygen consumption rate was maximal at about 12 hours after the start of culture.

After 54 hours of culture, the thus obtained culture liquids were diluted with sterile water, and then applied to ordinary bouillon agar media, followed by overnight static culture at 37° C. The numbers of the thus formed colonies were counted to count the numbers of cells. Furthermore, the previously prepared dilute solution was heated at 80° C. for 30 minutes and then similarly applied to an ordinary bouillon agar medium, followed by overnight static culture at 37° C. The number of the thus formed colonies was counted to count the number of heat-resistant bacteria. The sporulation rates were calculated from these results and shown in Table 7.

Furthermore, each of the obtained cultured media was centrifuged using a refrigerated centrifuge (TOMY SEIKO Co., Ltd. MX-307) at 10,000 rpm and 20° C. for 30 minutes, thereby collecting a supernatant.

To a solid-phase extraction column (Nihon Waters K.K. Oasis HLB 3 cc (400 mg) LP Extraction Cartridge), 6 mL of 0.1% TFA-containing acetonitrile was added and allowed to pass therethrough, and then 6 mL of 0.1% TFA-containing distilled water was added to pass through the column. Two mL of the thus collected centrifugal supernatant of each culture medium was added to pass through the column, and then 6 mL of 0.1% TFA-containing distilled water, and 6 mL of 0.1% TFA-containing acetonitrile/distilled water (20:80, v/v) were allowed to pass through the column in sequence for washing. Next, 5 mL of 0.1% TFA-containing acetonitrile/distilled water (90:10, v/v) was allowed to pass through the column, thereby collecting an eluate. 0.1% TFA-containing acetonitrile/distilled water (90:10, v/v) was added, so that the amount of the collected solution was 5 mL, and then HPLC analysis was conducted under the following conditions.

HPLC: Agilent Technologies, Inc. 1260 Infinity
Column: Nihon Waters K.K. XBridge C18 5 μm 4.6×250 mm
Mobile phase; A: 0.1% TFA-containing distilled water, B: 0.1% TFA-containing acetonitrile

| | |
|---|---|
| 0 to 3 minutes | A 80%/B 20% |
| 3 to 12 minutes | A 80%/B 20% → B 100% |
| 12 to 23 minutes | B 100% |
| 23 to 27 minutes | B 100% → A 80%/B 20% |
| 27 to 30 minutes | A 80%/B 20% |

Flow rate: 1 mL/min
Temperature: 40° C.
Detection: UV205 nm
Injection amount: 10 μL
Authentic sample: Iturin A from *Bacillus subtilis* (Merck)
Concentration: 30 ppm, 120 ppm
Solvent: 0.1% TFA-containing acetonitrile/distilled water (90:10, v/v)

Each medium was compared with the authentic sample in terms of peak area detected at the elution time of 12.1 minutes and that of 12.7 minutes, thereby calculating the iturin concentration in the culture medium.

Results are shown in Table 7.

TABLE 7

| | Test Result | |
|---|---|---|
| MEDIUM CONDITIONS | 2 | 2 + 4 |
| NUMBER OF CELLS (cfu/ml) | 1.23E+10 | 1.18E+10 |
| NUMBER OF HEAT-RESISTANT CELLS (cfu/ml) | 0.87E+10 | 1.21E+10 |
| SPORULATION RATE | 78.5% | 101.8% |
| ITURIN CONCENTRATION (ppm) | 149.5 | 319.8 |

In this culture test, about a 1.8-fold increase in bacterial concentration, about a 2.1-fold increase in iturin concentration, and an increase in the concentration of heat-resistant spores were confirmed in *Bacillus subtilis* cultured by fed-batch culture compared with *Bacillus subtilis* not cultured by fed-batch culture.

The invention claimed is:

1. A method for culturing a *Bacillus* bacterium, the method comprising:
   culturing a bacterium consisting of the *Bacillus* bacterium in a liquid medium in a fed-batch process, comprising feeding to the liquid medium from start of feeding to end of culturing a fed-batch medium comprising a sugar or a sugar-source raw material and a nitrogen-containing compound such that the fed-batch medium fed to the fed-batch process from the start of feeding to the end of culturing has a weight ratio of carbon atoms to nitrogen atoms of from 8.28 to 11.45,
   wherein a concentration of the sugar or the sugar-source raw material in the liquid medium is between 50.1 g/L and 100 g/L at a start of the culturing,
   wherein a total amount of the sugar or the sugar-sourced raw material fed by the fed-batch medium is 100 g or less per liter relative to the volume of liquid medium at the start of feeding, and
   wherein the *Bacillus* bacterium is selected from the group consisting of *Bacillus subtilis, Bacillus amyloliquefaciens, Bacillus pumilus, Bacillus simplex, Bacillus lentus, Bacillus laterosporus, Bacillus alvei, Bacillus popilliae, Bacillus licheniformis, Bacillus brevis, Bacillus stearothermophilus, Bacillus alcalophilus, Bacillus coagulans, Bacillus circulans, Bacillus siamensis, Bacillus lautus, Bacillus clausii, Bacillus thuringiensis, Bacillus cereus, Bacillus firmus, Bacillus velezensis, Bacillus pichinotyi, Bacillus acidocaldarius, Bacillus alkalicola, Bacillus azotoformans, Bacillus anthracis, Bacillus badius, Bacillus bataviensis, Bacillus cycloheptanicus, Bacillus aneurinilyticus, Bacillus migulanus, Bacillus abyssalis, Bacillus aestuarii,* and *Bacillus polymyxa.*

2. The method according to claim 1, wherein the feeding comprises feeding the fed-batch medium at a timing in a time period of from three hours to thirty hours after the start of the culturing.

3. The method according to claim 1, the method further comprising:
   heat-sterilizing a solution comprising the sugar or the sugar-source raw material and the nitrogen-containing compound, thereby producing the fed-batch medium.

4. The method according to claim 1, wherein the sugar or the sugar-source raw material is a non-reducing sugar.

5. The method according to claim 4, wherein the non-reducing sugar is at least one sugar selected from the group consisting of sucrose, trehalose, kestose, melezitose, gentianose, neobifurcose, fungitetraose, planteose, raffinose, stachyose, and bifurcose.

6. The method according to claim 1, wherein the nitrogen-containing compound is at least one compound selected from the inorganic nitrogen compound group consisting of an ammonium salt and ammonia, and the organic nitrogen compound group consisting of an amino acid, a peptide, a protein, urea, defatted soy flour, a soybean-derived component, a yeast-derived component, corn steep liquor, dry powder of corn steep liquor, a corn-derived component, an animal and plant protein and a hydrolysate thereof.

7. The method according to claim 1, wherein a dissolved oxygen concentration in the liquid medium is kept at 10% or more.

8. The method according to claim 1, further comprising:
controlling a growth of *Bacillus* bacteria by regulating a temperature of the liquid medium between 20° C. and 60° C.

9. The method according to claim 8, wherein the culturing comprises culturing the *Bacillus* bacterium at 28° C. to 32° C. during a logarithmic growth phase, and then culturing at 35° C. to 39° C.

10. The method according to claim 1, wherein the *Bacillus* bacterium is *Bacillus thuringiensis*.

* * * * *